United States Patent [19]
Saito et al.

[11] Patent Number: 6,020,171
[45] Date of Patent: *Feb. 1, 2000

[54] METHOD OF PREPARING PLASMID HAVING BOTH EXPRESSING ABILITY OF RETROVIRAL GENE AND PROCESSING ABILITY AFTER TRANSLATION, AND RESULTANT PLASMID AND EXPRESSION PRODUCTS THEREOF

[75] Inventors: Atsushi Saito, Kagawa; Hideo Shinagawa; Atsuo Nakata, both of Osaka, all of Japan

[73] Assignee: The Research Foundation for Microbial Diseases of Osaka University, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/684,187

[22] Filed: Jul. 19, 1996

Related U.S. Application Data

[62] Division of application No. 08/202,684, Feb. 25, 1994, Pat. No. 5,610,067, which is a continuation of application No. 07/809,489, Jan. 14, 1992, abandoned.

[30] Foreign Application Priority Data

May 28, 1990 [JP] Japan .................................. 2-139358

[51] Int. Cl.⁷ .......................... C12N 15/64; C12N 15/63; C12N 15/33
[52] U.S. Cl. .................. 435/91.4; 435/320.1; 536/23.72
[58] Field of Search ................................ 435/320.1, 69.1, 435/172.3, 91.4; 536/23.72

[56] References Cited

U.S. PATENT DOCUMENTS 5,093,241  3/1992  Bennett et al. ........................ 435/69.4

FOREIGN PATENT DOCUMENTS 0230222  7/1987  European Pat. Off. .

OTHER PUBLICATIONS

Guy et al. HIV F/3' orf encodes a phosphorylated GTP–binding resembling an oncogene product. Nature vol. 330 pp. 266–269, 1987.

Studier et al. Use of bacteriophage T7 polyberase to direct selective high–level expression of cloned genes J. Mol. Biol. vol. 189 113–130, 1986.

Wertman et al. Nucleotide sequence binding specificity of the lexA repressor of *Escherichia coli* J. Bact. vol. 163 376–384, 1985.

U. Ruther et al. et al. (1983) The Embo Journal 2(10): pp. 1791–1794.

S. Tabor et al. et al. (1985) Proc. Natl. Acad. Sci. USA 82: pp. 1074–1078.

G.C. Dubois et al. (1988) Aids Research and Human Retroviruses 4(6): pp. 419–431.

S.F.J. LeGrice et al. (1987) Gene 55: pp. 95–103.

A. Leuthardt et al. (1988) Gene 68: pp. 35–42.

C. DeBouck et al. (1987) Proc. Natl. Acad. Sci. USA 84: pp. 8903–8906.

S.R. Hammes et al. (1989) Proc. Natl. Acad. Sci. USA 86: 9549–9553.

*Primary Examiner*—John S. Brusca
*Attorney, Agent, or Firm*—Wenderoth, Lind & Ponack, L.L.P.

[57] ABSTRACT

The present invention provides a method of preparing a plasmid having both the ability of expressing retroviral genes and the ability of effecting the after-translational processing of the encoded products, and the resultant plasmid and the expression products thereof. The method of the present invention is to prepare a plasmid by insertion-linking a cDNA fragment containing at least the protease gene from among retroviral genes with a highly expressing gene or a gene direct expressing vector, thereby causing expression of the retroviral genes, and at the same time, to process said expression product itself with the protease in that expression product, thereby mass-producing three kinds of core protein encoded by vaq gene, and three kinds of enzymes encoded by pol gene, in the form of individual single mature or active proteins. Alternatively, the method of the present invention is to prepare a plasmid in which a cDNA fragment containing HIV nef gene region is inserted into a highly expressing gene and a gene direct expression vector, thereby mass-producing Nef protein which is the expression product of nef gene.

6 Claims, 2 Drawing Sheets

Reverse transcriptase activity of crude extraction liquid

Detection of reverse transcriptase and integrase by the Western blot technique

Eluation pattern of reverse transcriptase based on MonoQ column chromatography

Fraction of reverse transcriptase based on Affi-Gel Heparin chromatography

SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 1

Pro Ile Ser Pro Ile Glu Thr Val Pro Val Lys Leu Lys Pro Gly
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 2

Pro Ile Val Gln Asn Leu Gln Gly Gln Met Val His Gln Ala Ile
 1               5                  10                  15

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 3

Ile Gln Lys Gly Asn Phe Arg Asn Gln Arg Lys Thr Val
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 4

Gly Ala Arg Ala Ser Val Leu Ser Gly Gly Glu Leu Asp Lys Trp
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 5

Gly Gly Lys Trp Ser Lys Ser Ser Val Ile Gly Trp Pro Ala Val
 1               5                  10                  15

METHOD OF PREPARING PLASMID HAVING BOTH EXPRESSING ABILITY OF RETROVIRAL GENE AND PROCESSING ABILITY AFTER TRANSLATION, AND RESULTANT PLASMID AND EXPRESSION PRODUCTS THEREOF

This application is a divisional of application Ser. No. 08/202,684 filed Feb. 25, 1994, U.S. Pat. No. 5,610,067, which is a continuation of now abandoned application Ser. No. 07/809,489 filed Jan. 14, 1992.

BACKGROUND OF THE INVENTION

1. Field of the Invention

The present invention relates to a method of preparing an expression vector which permits simultaneous performance of the expression of retroviral genes and processing after translation, and the resultant plasmid and expression products available by such method of preparation. More particularly, the present invention relates to a method of preparing a plasmid, which causes expression of gag and pol genes of retrovirus by the application of recombinant DNA techniques, causes simultaneous processing of said expression product itself by a protease therein, and mass produces three kinds of core protein encoded by the gag gene, including p17, p24 and p15, and three kinds of enzymes encoded by pol gene, including protease, reverse transcriptase and integrase, individually and independently in the form of mature or active protein molecules, and the plasmid available by said method and expression products thereof. The present invention provides also a plasmid with a high expressing ability of nef gene and Nef protein molecule which is an expression product thereof.

2. Description of Related Art
1. Definition of Retrovirus

Retrovirus is the generic name of viruses classified as belonging to the retrovirus family and characterized by such common features as an envelope, a single-stranded RNA genome, and reverse transcriptase. This virus has a spherical shape having a diameter of 80 to 100 nm, the genome thereof consisting of two molecules of linear (+) stranded RNA with a molecular weight of about $3 \times 10^6$, these two molecules forming an inverted dimer.

More particularly, the retrovirus family is further classified into the following three subfamilies: oncovirus, lentivirus and spumavirus (R. E. F. Matthews Edt. "Classification and Nomenclature of Viruses-Fourth Report of the International Committee on Taxonomy of Viruses", pp 124–128, S. Karger [Swiss], 1982). Known viruses classed as oncoviruses, also named RNA tumor viruses, include human T cell leukemia virus, feline leukemia virus, murine sarcoma virus, moloney murine leukemia virus, bovine leukemia virus, hog leukemia virus, avian leukemia virus, avian sarcoma virus, avian myeloblastosis virus, and Rous associated virus. Known viruses classed as lentiviruses which are commonly known as viruses causing slow virus infection, include human immunodeficiency viruses types 1 and 2 (hereinafter respectively referred to as "HIV-1" and "HIV-2"), simian immunodeficiency virus, visna virus causing ovine encephalomyelitis, maedi virus causing jaagsiekte, caprine arthritic encephalitis virus, equine infectious anemia virus, and bovine lymphadenitis virus ("Current Topics of AIDS", vol. 1, pp. 95–117, John Wiley & Sons, 1987; Advances in Virus Research, vol. 34, p. 189–215, 1988). The viruses classed as spumaviruses, also named foamy viruses, infect such mammals as humans, monkeys, cattle, and cats. Foamy virus and syncytial virus isolated from these hosts are well known. The term retrovirus as used herein can be taken to include all viruses, known as well as unknown, characterized as retroviruses as described above.

2. Present Situation of Fundamental Research Regarding Retroviral Genes

Retroviruses are important not only from the point of view of the serious and often lethal infectious diseases which they cause in men and other animals, but they are also useful for the understanding of diseases such as sarcoma and for the preparation of material for use in research and genetic engineering. Consequently, much has been published in the literature about these viruses. As is well known, before 1980 retroviruses had been studied, as a model for the oncogenic mechanism, and had been implicated in a new and strange slow virus infectious disease which resulted in incurable secondary diseases. Since the identification of this disease as AIDS in the United States in 1981, comparative studies on various retroviruses have intensively been carried out using the full range of techniques in epidemiology, immunology, virology and molecular biology with a view to establishing methods for the treatment and prevention of AIDS. A huge volume of useful reports concerning AIDS has already been accumulated (Advances in Virus Research, vol. 34, pp. 189–215, 1988; Annual Review of Immunology, vol. 6.pp. 139–159, 1988; Microbial Pathogenesis, vol. 5, pp. 149–157, 1988; "HIV and Other Highly Pathogenic Viruses", pp. 33–41, Academic Press, Inc., 1988; "The control of Human Retrovirus Gene Expression", pp. 79–89, Cold Spring Harbor Laboratory, 1988; Cytological Engineering, vol. 7 (Suppl. 1), pp. S5-S15, 1988).

In the lentivirus the viral genome forms a complex with the reverse transcriptase, the structural protein and a primer tRNA, in the core of the viral particle. The viral genome comprises about ten different genes, including the basic three major genes encoding the viral particle components essential for virus multiplication, i.e., the gag (group-specific antigen) gene encoding the precursor of the core protein, the pol (polymerase) gene encoding a precursor of three different enzymes, and the env (envelope) gene encoding the precursor of the glycoprotein of the envelope. These genes are arranged from the 5' end to the 3' end in the sequence gag, pol, and env. Lentiviruses such as HIV also contain the unusual gene vif, and the genes are arranged in the specific sequence gag, pol, vif (previously called sor), env and nef. Part of the 5' end region of the pol gene overlaps about 240 bases with the 3' end region of the gag gene, and has a different reading frame. Frameshifting is thought to occur during translation of this overlapping portion. After translation of the precursor protein having a molecular weight of 55 kd from the entire aaq region of a total length of about 1.5 kb including that overlapping portion, there occurs cutting, i.e., processing by a protease, and it is considered to become three kinds of protein serving respectively as matrix protein, capsid and nucleocapsid, i.e., in the order of the enumeration given above, p17, p24 and p15. Expression of the entire pol gene region having a total length of about 3 kb produces the above-mentioned enzyme precursor (molecular weight: 100 kd) in the form of a fusion protein capable of being represented as $NH_2$—Protease—integrase—COOH, and then, this fusion protein itself is cut or cleaved under the effect of the existing protease produced by the virus or by the protease activity within the same molecule, and this process known as processing is considered to convert it into individual mature proteins (active proteins), i.e., individual enzymes including protease (p12), reverse transcriptase (p66 and p51) and integrase (p32) (Journal of Virology, vol. 62, No. 5, pp. 1808–1809, 1988).

All enzymes mentioned above play important roles in the viral multiplication process and in the process of infection, and the following functions have been confirmed or presumed. The protease participates in post-translational processing, core formation, and the maturation of the viral particle, and is highly specific towards the viruses from which it is derived. Reverse transcriptase is known to have three different enzymatic activities. Thus it functions as an RNA dependent DNA polymerase catalyzing the process of reverse transcription of the genomic RNA into DNA, which is the basic stage of the virus multiplication process. Simultaneously, the ribonuclease H activity of the enzyme specifically digests the RNA strand of the RNA-DNA heteroduplex which is formed, and the DNA dependent DNA polymerase activity produces double-stranded DNA. Reverse transcriptase is popularly used as a tool in genetic recombination. Integrase is an endonuclease acting on the DNA chain, and recognizes and catalyzes the excision of that part of the linear or circular virus double-stranded DNA, which has been transcribed from viral genomic RNA which is to be integrated into the host chromosome DNA, and is thus considered to participate in the process of provirus formation ("HIV and Other Highly Pathogenic Viruses", pp. 33–41, Academic Press, Inc., 1988; "The Control of Human Retrovirus Gene Expression", pp. 79–89; Cold Spring Harbor Laboratory, 1988; Cell Technology (in Japanese), vol. 7 (Suppl. 1), pp. S5–S15, 1988; AIDS Journal (in Japanese), vol. 1, No. 3, pp. 291–300, 1988; Aids, vol. 2 (Suppl. 1), pp. S29–40, 1988; KAGAKU-TO-SEIBUTSU (in Japanese), vol. 27, No. 4, pp. 218–227, 1989).

The region of nef gene having a total length of about 0.4 kb encodes a negative regulatory factor with a molecular weight of about 27 kd, and this regulatory factor is considered to stop multiplication of HIV by acting inhibitively on expression of HIV genome and thus is considered to be associated with latent infection ("Virology", edited by B. N. Fields et al., vol. 2, pp. 1534–1535, published by Raven Press [U.S.], 1990).

3. Present Status and Problems in Mass production of Retroviral Gene Products by Genetic Engineering Mass production of gene products (hereinafter referred to as "antigens") is widely conducted at various places in the world for the purpose of developing vaccines for human beings and animals and for the purpose of developing diagnostic drugs. As a typical example, the process for mass production of antigens of AIDS virus is outlined below. Principal antigens under study for mass production include precursor glycoprotein gp160 of env gene and processed products thereof, gp120 and gp41 ("Forefront of Countermeasures Against AIDS", edited and authored by Toshiaki Komatsu, vol. 2, pp. 477–495, published by CMC, 1989). For the production of gp160, for example, use is reported of vacuolovirus vector and insect cells (Proceedings of National Academy of Sciences (USA), vol. 84, pp. 6924–6928, 1987), recombinant vaccinia virus and BSC-40 or Hela cells (Nature, vol. 320, pp. 537–540, 1986; Nature, vol. 330, pp. 259–262, 1987), and adenovirus vector and A549 cells ("Vaccine 89", pp. 207–217, Cold Spring Harbor Laboratory, 1989). There have also been reported the expression of gp120 gene region by means of plasmid inserted and linked with that region and CHO cell line (Science, vol. 233, pp. 209–212, 1986), and production of gp120 with *Escherichia coli* (Science, vol. 234, pp. 1392–1395, 1986). In addition, known techniques regarding mass antigen production are classified and briefly listed below (hereinafter European Patent Provisional Publication No. is abbreviated as [EP], West German Patent Provisional Publication No. as [DE], United States Patent Application No. as [US], PCT International Patent Publication No. as [Wo], and French Patent Provisional Publication No. as [FR], respectively):

(1) Techniques aimed at mass expression of such genes as gag, pol, and env (hereinafter described for each host employed):

*Escherichia coli* (EP 331961, EP 322394, DE 3727137, DE 3724016, EP 293792, US 07/218304, US 07/110348, EP 255190, WO 87/07296, DE 3711016, EP 227169, EP 199301, EP 219106):

Yeast (DE 3804891, EP 322394,);

(2) Techniques for producing recombinant vaccinia virus inserted with such genes as gag, pol and env:

Japanese Patent Provisional Publication No. 1-148183, FR 2620030, FR 2607518, FR 2600079, FR 2587720, FR 2596711, EP 256677, WO 87/06260, WO 87/06262;

(3) Techniques for causing expression of env gene by virus vector:

Use of polyoma virus: Japanese Patent Provisional Publication No. 1-39991 and vacuolorivus: EP 272858, EP 265785; and (4) Techniques for causing expression of AIDS virus antigen as a fusion protein with hepatitis B virus antigen:

EP 278940

Apart from the production technique of recombinant virus applicable as an effective component of a live vaccine, for example, three elements including mass expression, secretion of gene products outside the host, and processing after translation are very important with a view to ensuring a low production cost and a high quality in industrial production of useful proteins by means of an expression vector. It is necessary to consider these three elements in constructing an expression vector. As is clear from the outline of the prior art techniques described above, mass expression has been studied by various researchers, and development of a secretory production system (Nippon Nogeikagaku Kaishi (in Japanese), vol. 60, No. 5, pp. 1035–1063, 1990) is widely and actively in progress. However, little attention is given by contrast to the contrivance of processing after translation despite its importance in saving labor in the refining process of gene products and improving purity of such products. It is therefore evident that development of an expression system allowing processing after translation has a valuable significance. Since Nef protein is useful in the field of diagnosis of AIDS and clarification of crisis mechanism, and therapy from the point of view of its antigenicity and functions, establishment of a mass production technique is expected.

SUMMARY OF THE INVENTION

For the purpose of overcoming the above-mentioned problems in the prior art techniques, the present inventors carried out extensive studies, and as a result, successfully caused mass expression of six kinds of protein encoded by gag and pol genes of retrovirus, and caused processing of them. More particularly, the present invention was completed by achieving preparation of a plasmid which permits mass production at a high and stable production yield with a low cost of the three kinds of viral core protein, pap gene products of retrovirus including p17, p24, and p15 and the three kinds of enzyme which are pol gene products including protease, reverse transcriptase and integrase, individually and independently in the form of mature or active protein molecules. This achievement was possible by preparing, by the full use of the recombinant DNA technology, a plasmid connected with fragments of gene cDNA of the virus prepared so as to contain the protease gene of retrovirus as an essential component through matching the translation frame within the inducible mass expression gene or within the gene direct expression vector, causing said plasmid to express the above-mentioned gene products at a high yield, and identifying processing of the gene product itself by the expressed protease. Direct expression means not causing the retroviral gene to indirectly express the desired protein in the form of a fusion protein with a different protein resulting from the gene being combined previously in the vector. Furthermore, the present inventors found it possible to obtain a transformant by introduction of the plasmid constructed through insertion and linkage of the above-mentioned gene cDNA into a host cell, and at the same time, to stably produce in a very large quantity the above-mentioned core proteins and enzymes encoded by said cDNA, not as fusion proteins but as respective mature proteins having a specific activity, in the culture product, by the application of a two-stage culture method described later for the culture of said transformant. In addition, the present inventors found that such processing was under the effect of the specific activity of the protease forming part of the fusion protein which was an expression product of the above-mentioned gene, i.e., said processing was a phenomenon intrinsic to the protease gene of retrovirus. The above-mentioned proteins thus processed were furthermore found to be easily mass produced and refined, with an excellent high purity and uniformity, and particularly with both an enzyme activity and antigenicity characterized by a very high substrate specificity unique to retrovirus. The present inventors achieved also mass production of Nef protein having a very specific antigenicity. The present invention was completed on the basis of these findings.

According to the present invention, there are provided a method for preparing a plasmid, which permits mass expression or mass production and processing of various kinds of proteins encoded by gag, pol, and nef genes, respectively, associated with retrovirus, and the resultant plasmid and expression products thereof. This plasmid and the core proteins, including p17, p24 and p15 and such enzymes as protease, reverse transcriptase, and integrase, and Nef protein which are the expression products of the plasmid are very useful as materials for research in the prevention and therapy of retroviral infectious diseases, as reagents in such fields as genetic engineering, protein engineering, molecular biology, in the development of pharmacotherapeutic drugs and antiviral agents against retroviral infectious diseases, and as antigens for the preparation of vaccines, diagnostic drugs and antibodies.

DETAILED DESCRIPTION OF THE INVENTION

Figure 1:
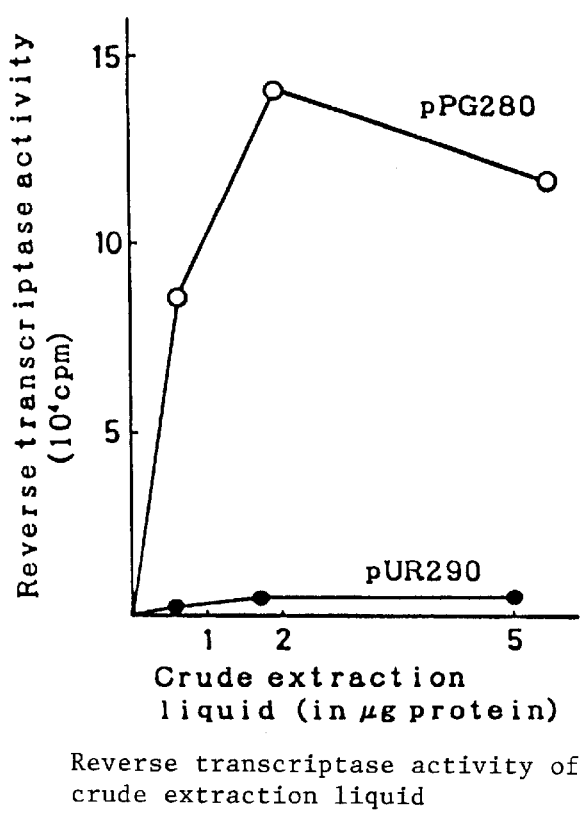
FIG. 1 is a graph illustrating titers of reverse transcriptase activity of crude extracts of *Escherichia coli* transformed with the plasmid pPG280 carrying the HIV pol gene, and *E. coli* transformed with vector pUR290 not having the HIV pol gene.

The present invention has the following features.
(I) Selection of retroviral genes and preparation of cDNA fragments:

As to retroviral genes, genes such as gag and pol of retrotranspozons can be used. More specifically, in the case of HIV, for example, genes within the gag region encoding core proteins, p17, p24 and p15, and genes within the pol region encoding protease, reverse transcriptase, and integrase are used. Expression of these genes requires the use of protease gene, and retroviral gene cDNA fragments prepared so as to contain, at least or at the shortest, the protease gene region from among the retroviral genes listed above as examples, are used through linkage in matching reading frame to a gene which is capable of being highly expressed. In the gene expression by the recombinant DNA technique, in which the retroviral genome is RNA, these genes are used after converting into complementary DNA. Such cDNA can be prepared by cloning either a proviral genome or the genomic DNA of an integrated virus. Alternatively, the requisite cDNA also can be obtained from cDNA libraries which have been prepared directly from genomic viral RNA using conventional techniques. However, any preparatory technique which relies on the direct use of a retrovirus carries an associated risk of infection. Therefore, in order to avoid the dangers associated with working directly with the virus and to save labor in the above-mentioned preparation processes, the use of a known and publically available cloned retroviral genomic cDNA is recommended. More particularly, as has previously been described, the cloning of various retroviral genomes, their sequencing, and preparation of restriction enzyme maps have already been reported by researchers throughout the world. Utilization of their achievement may be desirable on account of safety and convenience factors. The available clones include, for example, a plasmid pSRA2 (Journal of Virology, vol. 36, pp. 50–61, 1980) which carries the avian sarcoma virus genome; HIV-1 provirus genome clones, i.e., plasmids pNL3-1, pNL3-2 and pNL4-3 (Journal of Virology, vol. 59, pp. 284–291, 1986); HIV-1 pol gene clones, i.e., plasmid pNLH402 of *E. coli* strains UT 481/pNLH 402 (deposited at Fermentation Research Institute, Japan under the accession number FERM BP-2417), *E. coli* JM109/pCV91 (deposited at Fermentation Research Institute, Japan under the accession number FERM BP-3195), and *E. coli* JM109/pNLH122 (deposited at Fermentation Research Institute, Japan under the accession number FERM BP-3196). cDNA fragments can be prepared from these plasmids by conventional methods, for example, by digesting the DNA from the required region of above-mentioned plasmid clones by means of a restriction enzyme and purifying the resultant product through phenol extraction, chloroform treatment or ethanol precipitation. The restriction enzyme used for excision of DNA fragments may appropriately be selected by reference to the genomic DNA clone restriction enzyme map. Thus for example to excise DNA fragments from the entire pol gene region of the above-mentioned pNLH 402, the restriction enzyme HindIII (Journal of Virology, vol. 59, pp. 284–291, 1986) may be employed.
(II) Construction of retroviral gene expression plasmid, and preparation of transformant with ingression of the thus constructed plasmid:

The retroviral gene expression plasmid is constructed by introducing the retrovirus genomic cDNA fragments prepared as described above into a mass expression gene or a gene direct expression vector by a conventional method. The above-mentioned term "plasmid" used herein in relation to the present invention is used for a convenient notation and shall mean in a wide sense of the word, a replicon which expresses a retroviral gene. Therefore, any of the following known or commercially available expression vectors may be used to construct such a plasmid: plasmid vectors of the pSN508 series of the enteric bacteria family (U.S. Pat. No. 4,703,005); plasmid vector pJM105 (Japanese Patent Provisional Publication No. 62–286,930); vectors of the pBH103 series (Japanese Patent Provisional Publication No. 63–22,098) of yeast; attenuated varicella virus vector (Japanese Patent Provisional Publication No. 53–41,202); attenuated Marek's disease virus vector (European Patent Provisional Publication No. 334,530); Escherichia coli plasmid vector pUR290 series (EMBO Journal, vol. 2, pp. 1791–1794, 1983); pSN5182 (Journal of Bacteriology. vol. 157, pp. 909–917, 1984); and pT7—7 (Proceedings of the National Academy of Sciences [USA], vol. 82, pp. 1074–1078, 1985). What is important in the construction of the expression vector is to link the above-mentioned genes with a gene which is capable of being highly expressed. Thus, for example, when using plasmid pUR290 series referred to above, said genes should preferably be inserted downstream of the lacZ gene of the plasmid, or in the case of plasmid pSN5182, downstream of the plasmid pstS gene, or in the case of pT7—7, downstream of the oligopeptide gene resulting from pT7—7 under control of the T7 promoter. It is essential that the protease should be coexpressed with the target product through or not through the frameshifting. For example, in the case of the HIV-1, HIV-2, simian immunodeficiency virus or moloney murine leukemia virus where the protease is encoded in the pol gene region, the cDNA corresponding to the pol gene should be linked so as to match with the gene contained within the plasmid which have high expressing ability. On the other hand, the protease of avian sarcoma virus is encoded in the gag gene region which has a different reading frame from the pol gene, and similarly the protease gene of human T-cell leukemia virus or bovine leukemia virus has yet another reading frame differing from those of both the pol and gag genes. In these cases, care is needed to ensure significant expression of the retroviral genes. Suitable host cells which can be used to prepare transformants by introduction of the thus constructed expression vector include any cells which permit multiplication and expression of that expression vector, and simultaneously, from among such host cells, those permitting easy introduction of the constructed expression vector and certain detection thereof should be strictly selected for use. When using the above-mentioned pSN series plasmids as the expression vector, for example, it is desirable to use E. coli C75 strains (Microbiology Research Inst. Registration No. 10191) as the host cells, which permit selection of the transformant by the introduction of this vector, using drug resistance as the marker. When using the pUR290 series or pT7—7, it is desirable to employ E. coli UT481 (Journal of Bacteriology, vol. 163, pp. 376–384, 1985), or E. coli BL21 (DE3) (Journal of Molecular Biology, vol. 189, No. 1, pp. 113–130, 1986), which permit selection of the transformants by the introduction of these vectors, using ampicillin resistance as the marker. Introduction of the expression vector into such a host cell may be accomplished by conventional methods such as the calcium chloride method (Journal of Molecular Biology, vol. 53, pp. 154–162, 1977). A transformant obtained by introduction of the above-mentioned gag or pol gene expression plasmid is selected from positive colonies by the use of markers. Once a transformant colony has been identified the expression vector DNA is extracted and digested with a restriction enzyme, and the resulting DNA fragments are subjected to agarose gel electrophoresis. The size of the inserted DNA fragment can then be measured and the presence of a DNA fragment corresponding to the retroviral gene(s) confirmed. For example, when a DNA fragment comprising the entire pol gene region from plasmid pNLH402 is inserted into expression vector pUR290, an EcoRI fragment of about 4 kb DNA can be detected in restriction digests of DNA obtained from cells transformed with that vector.

(III) Confirmation of retroviral gene expression by clones of the transformed cells and mass production of various proteins by culture of the transformants:

Confirmation of retroviral gene expression by clones of the transformed cells can be accomplished, for example, by analyzing crude extracts of the cell by the Western blot technique. The crude extracts can be prepared, for example, by culturing and inducing the transformant in a conventional culture medium, collecting cells by low-speed centrifugation, treating the collected cells with sodium dodecyl sulfate and 2-mercaptoethanol, subjecting them to high-speed centrifugation, and collecting the supernatant liquid. The Western blot technique may be carried out in accordance with the conventional procedure using various commercially available materials in the following steps: subjecting the above-mentioned crude extract to polyacrylamide gel electrophoresis; transferring the separated protein onto a nitrocellulose membrane by the use of a transblotting apparatus; immersing the membrane into gelatin solution for blocking, and detecting the expressed protein, for example by means of its immunological reaction. Thus for example, when the specimen on the membrane is an HIV pol gene product, it may be detected by incubating the membrane with a primary serum obtained from a human HIV carrier, followed by washing and incubation with a secondary antibody comprising a peroxidase-conjugated marker anti-human IgG antibody. The presence of the pol gene product is detected by the development of a colored band upon addition of hydrogen peroxide solution and a chromogenic agent. Where the gene expressed originates from a retrovirus other than HIV, an appropriate retroviral antiserum is employed in place of the human HIV carrier serum as the primary serum, and an antibody to human or animal IgG is used as the secondary antibody.

Once expression of the gag or pol gene has been confirmed, mass production of various core proteins, and such enzymes as protease, reverse transcriptase and integrase, through culture of the transformant is achieved as follows. For the purpose of preparing the seeds for large-scale culture of that transformant, for example, when the transformant is an E. coli, the transformant is cultured in LB medium at a temperature of from 30 to 40° C. for from 12 to 35 hours until a bacteria concentration of from $2 \times 10^9$ to $8 \times 10^9$ cells/ml is reached. Then, inoculating such seeds into fresh medium prepared, and conducting main culture stage which takes place in two stages, a pre-culture and an after-culture. The pre-culture is carried out for the purpose of multiplying the cells and amplifying the expression vector, and is conveniently effected at a temperature of from 10 to 40° C. for from 1 to 24 hours, or more preferably at a temperature of from 15 to 37° C. for from 2 to 12 hours. The pre-culture is discontinued when a particular cell concentration is reached, for example, in the case of E. coli when the culture liquid reaches OD600$_{nm}$ of from 0.1 to 2.0. Subsequently, upon completion of this pre-culture stage, the culture system is shifted to the second, or after-culture stage. The conditions for the after-culture stage must be carefully selected to ensure that correct transcription and translation of genes and correct post-translational modification and processing of the gene product can take place to produce individual and single mature active proteins, and also to avoid degradation and inactivation of the desired gene products by the action of host proteolytic enzymes. The after-culture stage should preferably be carried out at a temperature lower than that in the pre-culture stage, i.e., at temperature of from 10 to 40° C. for from 1 to 40 hours, or more preferably, at a temperature of from 15 to 37° C. for from 3 to 35 hours. Depending upon the particular expression vector used, expression may be accelerated or induced, for example, by causing depletion of phosphate ion in the medium at the start of the after-culture stage or by adding an inducer into the medium. Application of the above-mentioned two-stage culture permits production of retroviral core proteins and such enzymes as protease, reverse transcriptase and integrase, not in the form of fusion proteins, but as independent active proteins, i.e., as individual and single mature proteins usually at a high yield of from 1 to 30 mg per liter of medium.

(IV) Purification of core proteins and such enzymes as protease, reverse transcriptase, and integrase:

This process can be accomplished by any combination of conventional methods. Suitable techniques included, for example: extraction of the synthesized protein through the use of precipitants; centrifugation of filtration product; preparation of crude extracts using ultrasonic treatment; high pressure treatment or a homogenizer to disrupt the cells; purification by adsorption elution on silica or activated charcoal, salting-out, or organic solvent-precipitation; and high-grade purification using ultracentrifugation, column chromatography or electrophoresis. For example the synthesized protein may be purified by fractionation by density-gradient centrifugation following adsorption-elution with silica and activated charcoal (Japanese Patent Provisional Publication No. 63–297).

The expression vector available by the method of the present invention may be provided in the form enclosed in an ampoule, a vial or other small container or introduced in a host. The core proteins and such enzymes as protease, reverse transcriptase and integrase mass produced by the expression vector of the present invention may be provided in the form of liquid, dried powder or adsorbed onto filter paper or a membrane, and enclosed in an ampoule, a vial or other small container. When provided in powder form, the protein may be reconstituted in the required amounts by appropriate dissolution in distilled water prior to use. When it is supplied adsorbed onto filter paper or a membrane, it should be used after wetting with a solution as prescribed in the instructions.

(V) Construction of nef gene expression plasmid; mass production, confirmation, purification and use of Nef protein:

These may be achieved by procedures similar to those enumerated in (I) to (IV) above. However, because the nef gene is located apart from gag and pol in HIV genome and production of Nef protein does not require processing after translation, it is more rational and has a labor-saving effect to produce this protein as a single protein. It is therefore possible to cause mass expression of nef gene as a single protein without taking account of processing in mass production of Nef protein. More specifically, the nef gene expression plasmid is prepared by insertion-linking nef gene cDNA fragments with a mass expression gene or a gene direct expression vector. The nef gene cDNA fragment may be prepared from plasmid pNL4-3 (Journal of Virology, vol. 59, pp. 284–291, 1986) or plasmid PNLH 152 (deposited at Fermentation Research Institute, Japan under the accession number FERM BP-3179) having a nef gene region in the HIV genome or nef gene cDNA.

The following benefits may be achieved by using the method of the present invention:

(1) According to the present invention, it is simultaneously possible to carry out mass expression and processing of retroviral genes. In mass production of retroviral antigen or enzyme using the expression vector, in which use of the very dangerous retrovirus itself is avoided, production is safe from the point of view of biohazard, and operation is easy.

(2) A very high production yield of the HIV proteins can be achieved, for example, from 1 to 30 mg protein per liter of bacterial culture, including various core proteins, enzymes and Nef protein.

(3) Whereby various core proteins, protease, reverse transcriptase, and integrase of retrovirus are ordinarily expressed as fusion proteins with mass expression gene products, these products can be produced using the present method, not in the state of fusion proteins, but as processed single mature proteins, so that the present method is more efficient and more practical than the single expression of the above-mentioned genes. Furthermore, taking into account the effects mentioned in (1) and (2) immediately above, such a process is also more economical, requiring lower production costs.

(4) Since the method of the present invention will make available at low cost and in a large quantity enzymes having a very high specificity for retroviral substrates and high-purity antigens of that virus, it can be expected to stimulate great progress not only in genetic engineering, but also in fundamental research on retrovirus infectious diseases such as AIDS, adult T cell leukemia, avian sarcoma or leukemia, and feline leukemia, the development of specific and selective therapeutic and preventive drugs, and diagnosis for these, and also to promote human health and hygiene and live-stock industry.

(5) The method of preparing the plasmid of the present invention, which permits mass expression and after-translational processing of various genes of retrovirus and various genes of transpozon, can be used to develop more efficient and rational mass production techniques for these gene products.

The method of the present invention will now be described in more detail with reference to the following non-limiting examples.

In the following Examples the activity of reverse transcriptase is determined as follows. A reaction mixture is made up comprising 50 mM tris-HCl(pH8.3), 50 mM potassium chloride, 10 mM magnesium chloride, 3 mM dithiothreitol, 0.1 w/V% NONIDET P-40 (made by Shell Oil [U.S.A.]), 20 µg/ml (rA)n(dT)$_{12-18}$ (Pharmacia [Sweden]), 0.5 mM dTTP (deoxythymidine triphosphate), and 1 Ci [$^3$H] dTTP (deoxythymidine triphosphate). 5 µl of sample is added to a total volume of 50 µl reaction mixture and is incubated at 37° C. for ten minutes. The mixture is then immediately cooled on ice, and filtered through a filter paper DE81 (made by Wattman[England]). The filter is washed well with 5% sodium phosphate solution, rinsed with water and then with ethanol and dried.

EXAMPLE 1

Construction of an Expression Vector Carrying the Pol Gene of Lentivirus

5 μg of plasmid pNL4-3 DNA (Journal of Virology, 59(2): 284–291, 1986) carrying the HIV proviral genome DNA was added to 5 μl HindIII, 20 μl 5×RM (50 mM tris-HCl [pH 7.5], 35 mM MgCl$_2$, 300 mM NaCl), diluted with distilled water to a total volume of 100 μl, and was incubated at 37° C. for an hour. The solution was then extracted with phenol saturated with TE(10 mM tris-HCl [pH 7.5], 1 mM EDTA). The water layer was treated with chloroform before ethanol precipitation. The precipitate was dissolved in 10 μl of TE and 1 μl of this solution was added to 0.1 μg (1 μl) of plasmid PHSG398 DNA which had been cleaved by HindIII and treated with alkaline phosphatase. 2 μl of 10×ligation buffer (660 mM tris-HCl [pH7.6], 66 mM MgCl$_2$, 100 mM DTT and 1 mM ATP), and 1 μl T4DNA ligase were further added and the total volume was brought up to 20 μl with distilled water. The mixture was incubated at 15° C. for 12 hours. E. coli strain JM103 was transformed with this reaction liquid in accordance with the calcium chloride method (Journal of Molecular Biology, 53: 154, 1970), and a chloramphenicol resistant colony was selected on an LB medium plate (1 W/V % Bacto-trypton, 0.5 W/V % Bacto-yeast extract, 1 W/V % NaCl and 1.5 W/V % agar) containing 20 μg/ml chloramphenicol. Plasmid DNA was extracted from the chloramphenicol resistant clone by a conventional method, and a clone pNLH402 was obtained by selecting a clone containing about 4.0 kb fragments originating from plasmid pNL4-3 DNA through HindIII excision.

HindIII in an amount of 5 μl and 5×RM in an amount of 10 μl were added to 5 μl (5 μg) of plasmid pNLH402 DNA, and the mixture was diluted with distilled water to a total volume of 50 μl. The mixture was incubated at 37° C. for an hour, and after phenol extraction and chloroform treatment, the mixture was subjected to ethanol precipitation. The resulting precipitate was added to 10 μl of 5×RM and 5 μl of BglII and was diluted with distilled water to a total volume of 50 μl, whereby it was completely dissolved. The mixture was incubated again at 37° C. for an hour, and after phenol extraction and chloroform treatment, the resulting product was subjected to ethanol precipitation. The thus obtained DNA was dissolved into 10 μl of TE.

At the same time, 5 μl of HindIII and 10 μl of 5×RM were added to 5 μg of expression vector pUR290 DNA (The EMBO Journal, 2 (2): 1791–1794, 1983). The mixture, diluted with distilled water to 50 μl, was incubated at 37° C. for an hour, and after phenol extraction, chloroform treatment and ethanol precipitation, 10 μl of 5×RM (NaCl concentration: 500 mM) and 5 μl or BamHI were added to it. 35 μl of distilled water were further added so as to cause complete dissolution of the precipitate, and the solution was then incubated at 37° C. for an hour. After phenol extraction and chloroform treatment, DNA precipitated with ethanol was dissolved into 10 μl of TE.

pUR290 DNA (1 μl) digested with HindIII and BamHI was mixed 111with pNLH402 DNA (1 μl) digested with HindIII and kglII, and 2 μl of 10 μligation buffer and 1 μl of T4DNA ligase were added. The volume was brought up to a total of 20 μl with distilled water, and was reacted at 15° C. for 12 hours. E. coli strain UT481 (Journal of Bacteriology, 163: 376–387, 1985) was transformed with the reaction liquid in accordance with the above-mentioned calcium chloride method. Ampicillin resistant colonies were selected on an LB medium plate containing 20 μg/ml ampicillin, and a clone containing fragments of about 3.8 kb originating from pNL4-3 was selected by measuring the size of the inserted fragment by EcoRI cleavage. Clone UT481/pPG280 (deposited at the National Institute of Bioscience and Human Technology, Ministry of International Trade and Industry, 1-3 Higashi 1-chome, Yatabe-machi, Tsukuba-gun, Ibaragi-ken, Japan on Mar. 28, 1994 and bears accession no. FERM BP-4622) was thus obtained. More specifically, in this clone the approximately 3.8 kb HIV pol gene region is considered to be ligated to the 3' end of lacZ gene of plasmid pUR290, and the lacZ and pol gene product is initially expressed as a fusion protein (about 230 kd), the various separate enzymes being produced after processing.

EXAMPLE 2

Figure 2:
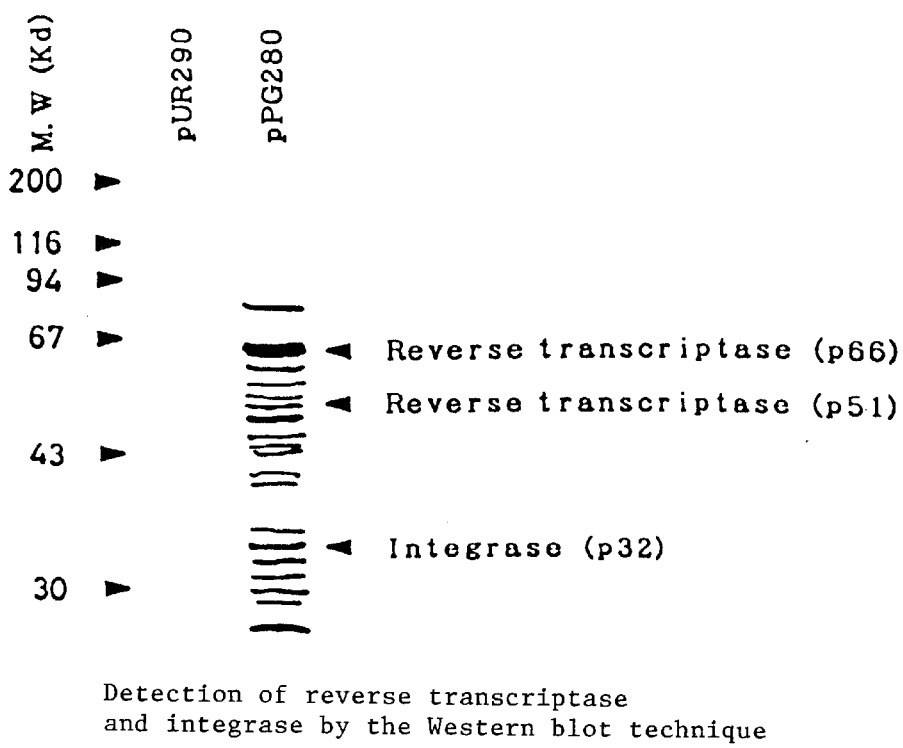
FIG. 2 is a graph illustrating the result of Western blot analysis using human serum obtained from HIV carriers, of crude extracts of *E. coli* transformed with plasmid pPG280 carrying the HIV pol gene and the vector pUR290 not carrying the HIV pol gene.
Figure 3:
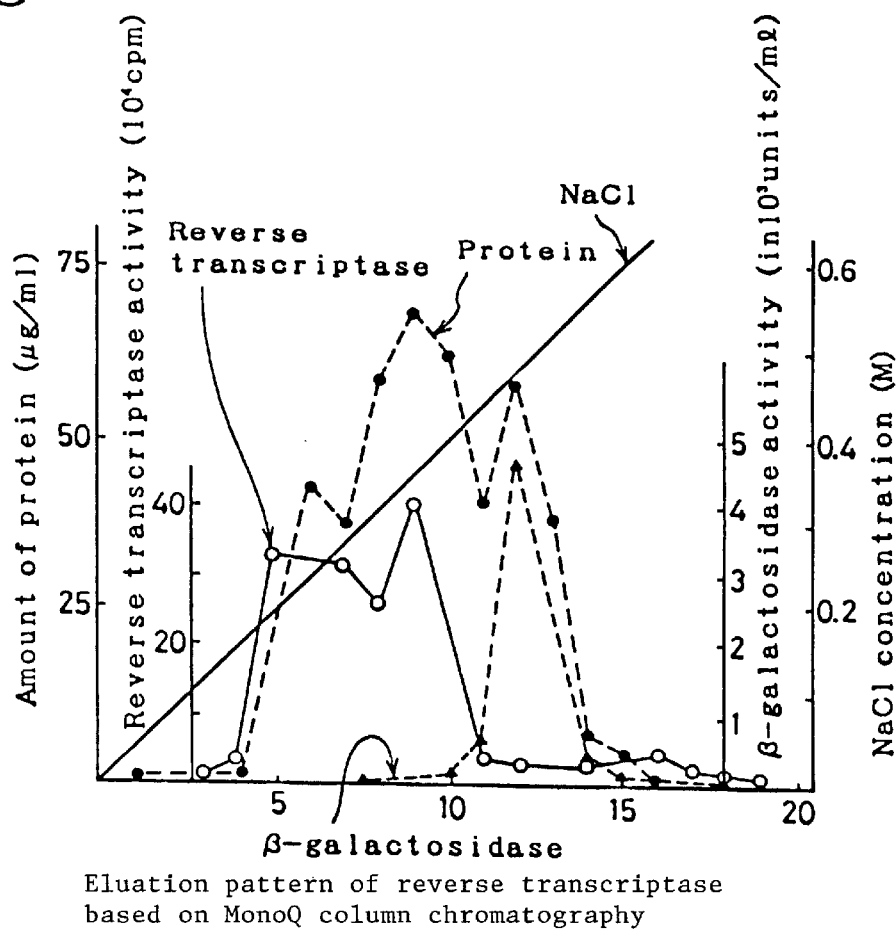
FIG. 3 is a graph illustrating the elution profile of reverse transcriptase derived from *E. coli* crude extracts on a MonoQ anion exchange column.

Production of Lentiviral Protease, Reverse Transcriptase and Integrase Enzymes by Culture of Transformed Cells The transformant clone UT481/pPG280 was cultured at 37° C. for 18 hours in LB medium containing 20 μg/ml ampicillin (1 W/V % Bacto-trypton, 0.5 W/V % Bacto-yeast extract and 1 W/V % NaCl). The resultant cells were added to fresh LB medium containing 20 μg/ml ampicillin at 1:100 dilution and pre-culture was carried out. When the OD600$_{nm}$ of the medium reached 0.5, 1 mM IPTG (Isopropyl-B-D-thiogalactopyranoside, from Sigma [U.S.A.]) was added, and culture was continued at 25° C. for 18 hours. Bacteria were collected by centrifugation (5,000 rpm for five minutes) and suspended in 1/25 volume of 40 mM tris-HCL (pH 8.0) (0.1 mM EDTA, 5 mM MgCl$_2$, 0.1 W/V % Triton X-100 and 10 mM 2-mercaptoethanol). After ultrasonic treatment (five 30-second bursts, 19.5kHz, 300 W), the supernatant liquid was separated by centrifugation (19,000 rpm, 60 minutes). To confirm the presence of HIV pol gene product in this crude extraction liquid, the activity of the reverse transcriptase in the crude extraction liquid was measured. The result is shown in FIG. 1. As expected, significant reverse transcriptase activity was observed. Analysis by the Western blot technique was also carried out: 4 W/V % sodium dodecyl sulfate (SDS) and 1 W/V % 2-mercaptoethanol were added to the collected bacteria cells. After boiling for five minutes and centrifugation (10,000 rpm for five minutes), the supernatant liquid was electrophoresed on a 0.1 W/V % SDS-10 W/V % polyacrylamide gel. After blotting onto a nitrocellulose membrane (made by S&S [West Germany]) by means of transblotting apparatus (made by BioRad [U.S.A.]), the membrane was immersed in 3 W/V % gelatin solution in accordance with the conventional blocking method. Then, as a primary reaction the membrane was incubated with human serum obtained from a HIV carrier, and after washing, as a secondary reaction was incubated with peroxidase marker-conjugated anti-human IgG serum (made by BioRad). Finally, after washing, the membrane was immersed in a chromogenic liquid prepared by adding 0.4 ml or DAB (3,3'-diaminobenzidine tetrahydrochloride) and 15 μl of 30 W/V % hydrogen peroxide solution to 50 ml of TBS (20 mM tris-HCL [pH 7.4]: 500 mM NaCl), to cause color formation, at room temperature for 15 minutes, and was then washed with distilled water. The result is shown in FIG. 2. While no specific band reacting with human HIV carrier serum was observed in the crude extraction liquid of cells transformed with a vector not carrying a HIV pol gene (E. coli strain UT481/pUR290, based on vector pUR290), bands of reverse transcriptase having molecular weights of 66 kd and 51 kd, integrase of 32 kd, and protease of 12 kd, i.e. the HIV pol gene products, were observed in the extraction liquid of transformed cells of strain UT481/pPG280. Column chromatography with the anion exchanger MonoQ (made by Pharmacia [Sweden]) indicates that the reverse transcriptase has been separated i.e. cleaved from the β-galactosidase as shown in FIG. 3, since the reverse transcriptase activity can be found in a fraction completely separated from β-galactosidase activity. This suggests that, although HIV pol gene products are produced as fusion proteins with β-galactosidase, protease, reverse transcriptase, and integrase regions of that fusion protein are specifically separated by the action of the protease which is itself a pol gene product, and accumulate in the cell.

EXAMPLE 3

Construction of a Vector to Enable the Production of Large Amounts of Lentiviral Protease 1 μl of HindIII and 10 μl of 5×RM were added to 5 μg of DNA of the pol gene expression plasmid pPG280 prepared in Example 1, and the mixture was diluted with distilled water to a total volume of 100 μl. The mixture was incubated at 37° C. for an hour, and after phenol extraction and chloroform treatment, the mixture was subjected to ethanol precipitation. The resultant precipitate was added to 5 μl of 5×RM (-NaCl) and 5 μl of BalI and was diluted with distilled water to a total volume of 50 μl, whereby the precipitate was dissolved. The mixture was incubated again at 37° C. for an hour, and after phenol extraction and chloroform treatment, the resulting product was subjected to ethanol precipitation. The resulting precipitate was added to 5 μl of 10×polymerase buffer (670 mM tris-HCl [pH 8.8], 67 mM $MgCl_2$, 166 mM $(NH_4)_2SO_4$, 100 mM 2-mercaptoethanol and 67 μM EDTA), 5 μl of 10×dNTP solution (each 3.3 mM of DATP, dGTP, dTTP, and dCTP) and 1 μl T4 DNA polymerase and was diluted with distilled water to a total volume of 50 μl, whereby it was dissolved. The mixture was incubated at 37° C. for 15 minutes, and after phenol extraction and chloroform treatment, the resulting product was subjected to ethanol precipitation. To the mixture of 1 μl of the solution prepared by dissolving the resultant precipitation into 10 μl of TE and 2 μl of 10×ligation buffer, 1 μl of T4DNA ligase was further added and total volume was brought to 20 μl with distilled water. The mixture was further incubated at 15° C. for 12 hours. *E. coli* strain UT481 was transformed with this reaction liquid in accordance with the above-mentioned calcium chloride method. An ampicillin resistant colony was selected on an LB medium plate containing 20 μg/ml ampicillin, and a clone containing 0.55 kb fragments originating from pNL4-3 was selected by measuring the size of the inserted fragment using EcoRI digestion. Clone UT481/pLB550-3 was thus obtained.

Construction of a vector for mass production of protease of HIV-1 (lentivirus):

pNLH402 (Example 1) was excised with B1II and KDnI, and the resultant about 1.7 kb DNA fragment was excised further with NlaIV. The thus prepared about 1.2 kb DNA fragment was inserted into HincII portion of the cloning vector pCU19, to obtain pUN40. The thus obtained pUN40 was excised with BamHI and PstI, and the resultant 1.2 kb DNA fragment was inserted into the expression vector pUR291 (The EMBO Journal, 2 (2): 1791–1794, 1983) and pT7-7 (Proc. Natl. Acad. Sci., USA, 82: 1074–1078, 1985) cleaved with BamHI and PstI to construct pPG401 and pTP440, respectively. Then, pPG401 was excised with BalI and PstI, and after T4 DNA polymerase treatment, caused to make self-linkage to obtain pPG421. On the other hand, pTP440 was excised with BalI and PstI, and after T4 DNA polymerase treatment, caused to make self-linkage to obtain pTP442. These pPG401, pPG421, pTP440 and pTP442 express protease of HIV-1. For pPG401 and PPG421, strains UT481 and JM103 were used as the hosts for expression. For pTP440 and pTP442, strain BL21 (DE3) was employed as the host for expression.

EXAMPLE 4

Mass Production of Lentiviral Protease by Transformed Cells

Transformant clone UT481pLB550-3 was cultured at 37° C. for 18 hours in LB medium (containing 20 μg/ml ampicillin). The resulting cells were added to fresh LB medium (containing 20 μg/ml ampicillin) at 1:100 dilution and pre-culture was carried out at 37° C. When the $OD600_{nm}$ of the medium reached 0.5, 1 mM IPTG (Isopropyl β-D-thiogalactopyranoside, Sigma [U.S.A.]) was added, and culture was continued at 37° C. for 6 hours. Bacteria were collected by centrifugation (5,000 rpm for five minutes), and 4 W/V % sodium dodecyl sulfate (SDS) and 1 W/V % 2-mercaptoethanol were added. After boiling for five minutes and centrifugation (10,000 rpm for five minutes), the supernatant liquid was electrophoresed on a 0.1 W/V % SDS—15 W/V % polyacrylamide gel. Subsequently, the collected bacteria were analyzed by means of the Western blot technique described in Example 2. While no specific band reacting with human HIV carrier serum was observed in crude extracts of UT481/pUR290, bands of 12 kb protease were observed in the extraction liquid of UT481/pLB550-3. Especially, pLB550-3 produced an amount of protease several times as much as pPG280. In this clone, 0.55 kb HIV pol gene is thought to be ligated to the 3' end of lacZ gene of plasmid pUR290, and the lacZ-pol gene product is thought to be produced as a fusion protein with molecular weight of about 140 kb, a protease of about 12 kb being produced after processing.

EXAMPLE 5

Construction of an Expression Vector Carrying Oncoviral Protease and Pol Gene

5 μg of plasmid pSRA2 DNA carrying Rous sarcoma virus cDNA (Journal of Vipology, 36, pp. 50–61, 1980) was added to 5 μl of BamH1 and 20 μl of 5×RM, and was diluted with distilled water to a total volume of 100 μl, which was then incubated at 37° C. for an hour. After this reaction, the mixture was electrophoresed on a 1 W/V % agarose gel having a low melting point, and the gel portion containing a 1.8 kb DNA fragment was digested. Then, after phenol extraction and chloroform treatment, the resulting product was subjected to ethanol precipitation. The precipitate was dissolved in 10 μl of TE and 1 μl of this solution was added to 0.1 μg (1 μl) of plasmid pUR291 DNA which had been cleaved by BamH1 and treated with alkaline phosphatase. 2 μl of 10×ligation buffer, and 1 μl of T4 DNA ligase were further added and the total volume was brought up to 20 μl with distilled water. The reaction mixture was then incubated at 15° C. for 12 hours. Subsequently, *Escherichia coli* UT481 strain was transformed with this reaction mixture in accordance with the calcium chloride method, and an ampicillin resistant colony was selected on an LB medium plate containing 20 μg/ml ampicillin. Plasmid DNA was extracted from the ampicillin resistant clone using a conventional method, and a clone pSR281 was obtained by selecting a clone containing a 1.8 kb fragment originating from plasmid pSRA2 and producing a lacZ-gag fusion protein. 5 μg of plasmid pSRA2 DNA was added to 5 μl or PstI and 20 μl of 5×Rm (750 mM NaCl), and was diluted with distilled water to a total volume of 100 μl, which was then incubated at 37° C. for an hour. After this reaction, the mixture was electrophoresed on a 1 W/V % agarose gel having a low melting point, and a 1.8 kb DNA fragment was digested. Then, after phenol extraction and chloroform treatment, the resulting product was subjected to ethanol precipitation and dissolved to 10 μl of TE. Similarly, the double-stranded phage DNA of M13mP18 was cleaved by PstI and treated with alkaline phosphatase. A 1 μl (0.1 μg) of this DNA was added to 1 μl of the 3.1 kb DNA fragment mentioned above, 2 μl of 10×ligation buffer and 1 μl of T4DNA ligase, and was diluted with distilled water to total volume of 100 μl, which was then incubated at 15° C. for 12 hours. Subsequently, the recombinant phage DNA was used to transfect *E. coli* strain TG1 following the calcium chloride method, and a plaque was formed on a 2YT medium plate (1.6 W/V % Bacto-trypton, 1 W/V % Bacto-yeast extract, 0.5 W/V % NaCl and 1.5 W/V % Bacto-agar) containing an X-gal (5-bromo-4-chloro-3-indolyl-β-D-glactopyranoside, Sigma [U.S.A.]).

The transfected TG1 strain was propagated in a 2YT medium (1.6 W/V % Bacto-trypton, 1 W/V % Bacto-yeast extract, and 0.5 W/V % NaCl) until the $OD600_{nm}$ of the medium reached 0.3, and some of the achromatic clone of the resultant plaque were inoculated. Incubation was continued for several hours and then single- and double-stranded DNA were prepared in accordance with conventional methods. A clone M13sr31 which contains a 3.1 kb fragment originating from pSRA2 was selected by digesting the obtained double-stranded DNA with PstI and BamHI. The 3.1 kb fragment originating from pSRA2 encodes the 3' end of the gag gene, the termination codon TAG, and the pol gene. The insertion of one base before the termination codon results in the expression of a gag-pol fusion gene having matching translation frames. Thus by using an in vitro mutagenesis kit (made by Amersham[England]), a clone M13sr32 was obtained, containing the sequence ATAG obtained by inserting one base before the termination codon TAG on the M13sr31.

5 μg of double-stranded DNA of M13sr32 was added to 5 μl of PstI and 20 μl of 5×RM, and was diluted with distilled water to total volume of 100 μl, which was then incubated at 37° C. for an hour. After this reaction, the mixture was electrophoresed on a 1 W/V % agarose gel having a low melting point, and a gel containing a 3.1 kb DNA fragment was digested. After phenol extraction and chloroform treatment, the resulting product was subjected to ethanol precipitation. The precipitate was dissolved in 10 μl of TE and 1 μl of this solution was added to 1 μl (0.1 μg) of plasmid pSR281 DNA (see earlier) digested by PstI and treated with alkaline phosphatase. 2 μl of 10×ligation buffer, 1 μl of T4 DNA ligase were further added and the total volume was brought up to 20 μl with distilled water. Then, the mixture was incubated at 15° C. for 12 hours. Subsequently, *Escherichia coli* UT481 strain was transformed with this reaction mixture in accordance with the calcium chloride method, and an ampicillin resistant colony was selected on an LB medium plate containing 20 μg/ml ampicillin. Plasmid DNA was extracted from the ampicillin resistant clone by a conventional method, and the presence and direction of the 3.1 kb fragment originating from M13sr32 were confirmed by digesting the plasmid by PstI and BamHI, and then a clone UT481/pSR271 which was assumed to express protease and pol gene products was obtained.

In the 1.8 kb region originating from pSRA2, and contained in plasmid pSR281, a 1.3 kb region overlapping with 3.1 kb fragment originating from M13sr32 was removed when pSR281 was cleaved with PstI.

EXAMPLE 6

Production of Oncoviral Protease, Reverse Transcriptase and Integrase

Transformant clone UT481/pSR271 was cultured at 37° C. for 18 hours in an LB medium (containing 20 μg/ml ampicillin), the resultant cells were added to fresh LB medium (containing 20 μg/ml ampicillin) at 1:100 dilution and pre-culture was carried out. When the $OD600_{nm}$ of the medium reached 0.5, 1 μmM IPTG was added, and culture was continued at 25° C. for 18 hours. Bacteria were collected by centrifugation (5,000 rpm for five minutes) and suspended in 1/25 volume of 40 mM tris-HCl (pH 8.0) (0.1 mM EDTA, 5 mM $MgCl_2$, 0.1 W/V % Triton X-100 and 10 mM 2-mercaptoethanol). After ultrasonic treatment (five 30-second bursts, 19.5 kHz, 300 W), the supernatant was separated by centrifugation (19,000 rpm, 60 minutes). To confirm the presence of RSV gene product in this crude extraction liquid, the activity of the reverse transcriptase in the crude extraction liquid was measured. As expected, significant reverse transcriptase activity was observed. Analysis by the Western blot technique was also carried out: 4 W/V % sodium dodecyl sulfate (SDS) and 1 W/V % 2-mercaptoethanol were added to the collected bacteria. After boiling for five minutes and centrifugation (10,000 rpm for five minutes), the supernatant was electrophoresed on a 0.1 W/V % SDS—15 W/V % polyacrylamide gel. After blotting onto a nitrocellulose membrane (made by S&S [West Germany]) using transblotting apparatus (made by BioRad [U.S.A.]), the membrane was immersed in a 3 W/V % gelatin solution in accordance with the conventional blotting method. Then, as a primary reaction the membrane was incubated with anti-RSV rabbit serum, and after washing, as a secondary reaction was incubated with peroxidase marker conjugated anti-rabbit IgG serum (made by BioRad). Finally, after washing, the membrane was immersed in a chromogenic liquid prepared by adding 0.4 ml of DAB (3,3'-diaminobenzidine tetrahydrochloride) and 15 μl of 30 W/V % hydrogen peroxide solution to 50 ml of TBS (20 mM tris-HCl [pH 7.4], 500 mM NaCl), to cause color formation, at room temperature for 15 minutes, and was then washed with distilled water. While no specific band reacting with anti-RSV rabbit serum was observed in the crude extraction liquid of the transformed cell UT481/pUR290 (based on the vector pUR290 not having a RSV gene), bands of RSV reverse transcriptase were observed in the extraction liquid of UT481/pSR271. Although RSV protease and the pol gene product are produced as fusion proteins with the β-galactosidase, the protease and reverse transcriptase regions are specifically separated by the action of the protease which is itself a paa gene product, and are thought to be accumulated in the cell. In the clone UT481/pSR271, the 3.6 kb Rous sarcoma virus gag and pol gene region is thought to be ligated to the 3' end of the lacZ gene of plasmid pUR291, and it is suggested that the lacz, gag and pol gene products are expressed as a fusion protein (about 230 kb), which is then processed to liberate the enzymes e.g. the protease (P15), reverse transcriptase (P92, P65) and integrase (P32).

EXAMPLE 7

Extraction of Reverse Transcriptase

As mentioned above in Example 2, transformed *E. coli* clone UT481/pPG280 was cultured in 9 1 LB medium (containing 20 µg/ml ampicillin) at 25° C., and when the culture reached an OD600$_{nm}$ of 0.5, 1 mM IPTG was added. Culture was further continued for another 24 hours, and after collection, the cells were suspended in 120 ml of 40 mM tris-HCl (pH 8.0) (containing 0.1mM EDTA, 5 mM MgCl$_2$, 0.1 W/V % Triton X-100 and 10 mM 2-mercaptoethanol) buffer. Bacteria cells were disrupted by ultrasonic treatment and subjected to centrifugation (19,000 rpm for 60 minutes), and the supernatant was separated as the crude extraction liquid.

EXAMPLE 8

Purification of Reverse Transcriptase

Polymine P (made by BRL[U.S.A.]) was added in an amount of 0.1 W/V % to the crude extraction liquid, which was then stirred at 4° C. for 30 minutes and centrifuged (16,000 rpm for 20 minutes).

Ammonium sulfate was added to the supernatant. The precipitate produced from this 40% saturated solution was removed by centrifugation (16,000 rpm for 20 minutes) and 137 ml of supernatant liquid obtained. Ammonium sulfate was added again to 80% saturation, and the thus produced precipitate was dissolved in 50 ml of the above-mentioned 40 mM tris-HCl buffer and was then dialyzed against the same buffer containing 50 mM NaCl.

EXAMPLE 9

High Grade Purification of Reverse Transcriptase

Figure 4:
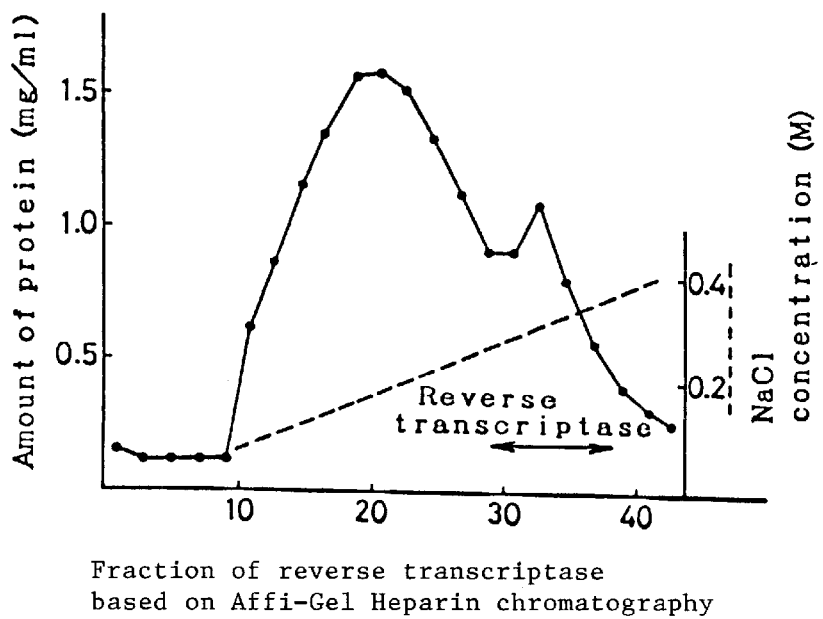
FIG. 4 is a graph illustrating purification of reverse transcriptase by fractionation using Affi-Gel Heparin chromatography.

High grade purification was carried out using DEAE Bio-Gel A (BioRad [U.S.A.]) and Affi-Gel Heparin column chromatography (BioRad). The dialyzed sample of Example 8 was applied to a 30 ml DEAE Bio-Gel A column equilibrated with 40 mM tris-HCl (pH 8.0) (containing 0.1 mM EDTA, 5 mM MgCl$_2$, 0.1 W/V % Triton X-100, 10 mM 2-mercaptoethanol and 50 mM NaCl). The eluted sample was then applied to a 30 ml Affi-Gel Heparin column equilibrated with the above-mentioned buffer and was eluted with 150 ml buffer comprising a sodium chloride gradient of from 50 mM to 40 mM. The result is shown in FIG. 4. Fractions 29 to 38 containing reverse transcriptase activity were pooled. The pooled fractions were dialyzed against 20 mM sodium phosphate buffer (pH 6.8) (containing 0.1 mM EDTA, 5 mM MgCl$_2$, 0.1 W/V % Triton X-100 and 10 mM 2-mercaptoethanol) and were further purified by HPLC on a hydroxyapatite column (KB column, Koken [Japan]). Specifically, after adsorption of the sample onto the column, elution was carried out with a linear gradient of sodium phosphate of 20 to 40 mM, and fractions containing reverse transcriptase activity were pooled. Purified reverse transcriptase was thus obtained. The thus obtained reverse transcriptase was confirmed, by the use of SDS PAGE, to have a purity of over 95%. The yield was 31% relative to the crude extraction liquid. The purified reverse transcriptase consisted of p64 and p51 having substantially the same molar ratios, and determination of the N-terminal amino acid sequence of both subunits showed:

Pro-Ile-Ser-Pro-Ile-Glu-Thr-Val-Pro-Val-Lys-Leu-Lys-Pro-Gly . . . (SEQ ID NO:1, thus agreeing with the amino acid sequence predicted from the nucleotide sequence.

EXAMPLE 10

Construction of a Vector Highly Expressing Core Proteins of AIDS Virus

DNA of plasmid pNL4-3 (Journal of Vipology, 59 (2): 284–291, 1986) carrying HIV-1 proviral genome DNA was excised with PvuII, and resultant about 2.1 kb DNA fragment was collected. This fragment was inserted into the HincII portion of plasmid pUC9. The fragment thus introduced, the 5' end of which was connected to the BamHI portion side was referred to as pCV91.

After excising pCV91 with BamHI and BalI, the resultant about 1.5 kb DNA fragment was collected and inserted into an expression vector pUR292 (The EMBO Journal, 2 (2): 1791–1794, 1983) having sequentially been treated with SalI, T4 DNA polymerase and BamHI to prepare pPG912. Furthermore, pPG912 was excised with BqlII, and after T4 DNA polymerase treatment, caused to make self-linkage to convert pPG912 into pPG922 in which four bases were introduced at BalII portion.

In pPG912 and pPG922, a DNA fragment completely containing all the range from p24 region of HIV-1 gag gene region to the protease region of pol gene was connected in-frame to the 3' end of lacZ gene. The gene product of HIV-1 was expressed as a fusion protein with β-galactosidase, and then, subjected to a process based on protease expressed, via frameshifting from gag to pol for pPG912, or without frameshifting for pPG922, producing core protein p24. In pPG912, p15 was also produced.

After excising the above-mentioned expression plasmids pPG912 and pPG922 with BamHI and ClaI, the resultant about 1.5 kb DNA fragments were collected and introduced into an expression vector pT7-7 (Proc. Natl. Acad. Sci., USA, 82: 1074–1978, 1985) cleaved with BamHI and ClaI to prepare pTG11 and pTG12. Then, pTG11 and pTG12 were cleaved with BamHI, treated with T4 DNA polymerase, and caused to make self-linkage to prepare pTG110 and pTG120. This expresses the HIV protein region identical with the source pPG912 and pPG922 as fusion proteins with oligopeptide resulting from pT7-7 under contpol of the T7 promotor. The fusion proteins were subjected to a process using protease, leading to production of p24 and p15.

As the host for constructing plasmid, E. coli strain JM103 (Nucleic Acid Research, 9 (2): 309–321, 1981) was used; E. coli strain UT481 (Journal of Bacteriology, 163: 376–384, 1985) was used as the host for protein expression for pPG912 and pPG922; and E. coli strain BL21 (DE3) (Journal of Molecular Biology, 189 (1): 113–130, 1986) was used as the host for protein expression for pTG100 and pTG120. The respective yields of purified p24 and p15 per liter of E. coli culture are shown in Table 1.

EXAMPLE 11

Construction of a Vector Highly Expressing Nucleoprotein of AIDS Virus

The gag-pol gene expressing plasmid pPG912 as prepared in Example 10 was excised with HindIII to recover the resultant about 0.9 kb DNA fragment. Then, plasmid pPG930 was prepared by introducing this fragment in a desirable direction into the HindIII portion of the expression vector pUR290 (The EMBO Journal, 2 (2): 1791–1794, 1983). In pPG930, the DNA fragment completely containing all the range from p15 region of HIV-1 gag region to the protease region of pol gene was in-frame-linked to the 3' end of LacZ gene on pUR290. HIV gene product was expressed as a fusion protein with β-galactosidase. This fusion protein was subjected to a process based on protease expressing via frameshifting, resulting in production of p15 nucleoprotein.

Another plasmid pTG21 was prepared by introducing in a desirable direction the above-mentioned 0.9 kb HindIII fragment into HindIII portion of the expression vector pT7-7. Furthermore, pTG21 was excised with SalI, and after T4 DNA polymerase treatment, caused to make-linkage to obtain pTG210, which expresses the same HIV protein region as that of pPG930 as a fusion protein with oligopeptide resulting from pT7-7 under contpol of the T7 promotor. This fusion protein was subjected to a process based on protease expressing through frameshifting, thus producing p15.

As the host for constructing the plasmid, strain JM103 was used; strain UT481 was used as a host for protein expression for pPG930; and strain BL21 (DE3) was used as the host for protein expression for pTr210. The respective yields of purified p15 per liter of E. coli culture are as shown in Table 1.

TABLE 1

| Yield of purified protein per liter of culture | | | |
|---|---|---|---|
| Expression Plasmid | Host | p24 (mg) | p15 (mg) |
| pPG912 | UT481 | 5 | 0.7 |
| pPG922 | UT481 | 5 | — |
| pPG930 | UT481 | — | 1 |
| pTG110 | BL21(DE3) | 19 | 3 |
| pTG120 | BL21(DE3) | 10 | — |
| pTG210 | BL21(DE3) | — | 5 |

Determination of the N-terminal amino acid sequences for purified p24 and p15 showed: Pro-Ile-Val-Gln-Asn-Leu-Gln-Gly-Gln-Met-Val-His-Gln-Ala-Ile . . . (SEQ ID NO:2) for p24, and Ile-Gln-Lys-Gly-Asn-Phe-Arg-Asn-Gln-Arg-Lys-Thr-Val . . . (SEQ ID NO:3) for p15, thus agreeing with the amino acid sequences predicted from the respective nucleotide sequences.

EXAMPLE 12

Extraction of Core Protein p24 of AIDS Virus by Culture of Transformant

The transformant clone UT481/pPG922 was cultured for 18 hours at a temperature of 37° C. in an LB medium (1 W/V % Bacto-tryptone, 0.5 W/V % Bacto-yeastextract and 1 W/V19 NaCl) containing 20 μm/ml ampicillin, then 1/100 polume was added to a fresh LB medium (containing 20 μm/ml ampicillin), and was pre-cultured at a temperature of 37° C. When the OD600$_{nm}$ of the medium reached 0.5, 1 mM IPTG (Isopropyl-thiogalactoside made by Sigma [US]) was added, and culture was continued at a temperature of 37° C. for eight hours. Bacterial cells were collected through centrifugation (5,000 rpm for 10 minutes), suspended on 50 mM sodium phosphate [pH 7.0], and after ultrasonic treatment (five 3-minute bursts, 19.5 kHz, 300 W), supernatant liquid was separated by centrifugation (19,000 rpm for 60 minutes).

Rough purification of p24: Ammonium sulfate was added to crude extraction liquid so as to achieve 35% saturation, then after stirring, the precipitate obtained through centrifugation (16,000 rpm, for 20 minutes) was dissolved into 30 ml:20 TM sodium malonate [pH 5.3] and dialyzed in the resultant liquid.

Purification of p24: The dialyzed sample was passed through MonoS column (made by Pharmacia [Sweden]) equilibrated with 20 mM sodium malconate [pH 5.3], and eluted with sodium chloride gradient (from 0 to 1M). The fraction containing p24 was pooled and dialyzed against 20 mM tris-HCl buffer [pH 8.4]. After dialysis, the liquid was applied to MonoQ column (made by Pharmacia [Sweden]) equilibrated with the buffer mentioned above, and eluted with sodium chloride gradient (from 0 to 1M) to obtain purified p24.

EXAMPLE 13

Extraction of p15

The transformant clone BL21 (DE3)/pTG210 was cultured at 37° C. for 18 hours in LB medium containing 20 μg/ml ampicillin, then 1/100 volume was added to fresh LB medium (containing 20 μg/ml ampicillin) and cultured at 37° C. When the OD600$_{nm}$ the medium reached 0.5, 1 mM IPTG was added, and culture was continued at 37° C. for five hours. Bacterial cells were collected and suspended in 1/50 polume of 20 mM sodium phosphate [pH 7.0], and after ultrasonic treatment (six 30-second bursts, 19.5 kHz, 300 W), the supernatant was separated by centrifugation (19,000 rpm, 60 minutes) as the crude extraction liquid.

Rough purification of p15: Ammnonium sulfate was added to the crude extraction liquid so as to achieve 60% saturation, and after stirring, the mixture was subjected to centrifugation (16,000 rpm, 20 minutes). The resultant precipitate was dissolved into 20 mM sodium phosphate buffer [pH 7.0] and was then dialyzed against same buffer.

Purification of p15: The dialyzed sample was applied to a phosphocellulose column (made by Wattman [UK]) equilibrated with 20 mM sodium phosphate [pH 7.8]. The sample was then eluted with sodium chloride gradient of from 0 to 1M. Fractions containing p15 were pooled and dialyzed against 20 mM sodium phosphate buffer [pH 7.0]. The dialyzed sample was applied to hydroxyapatite column (KB column, made by Koken, Ltd.), and eluted with sodium phosphate gradient of from 20 to 70 mM. The fractions containing p15 were pooled and dialyzed against 20 mM sodium phosphate buffer [pH 7.0]. This sample was then applied to MonoS column, and eluted with sodium chloride gradient of from 0 to 1M. The fractions containing p15 were pooled to obtain purified p15.

EXAMPLE 14

Construction of Expression Plasmid Carrying Gag-pol Genes of AIDS Virus

HIV-1 proviral DNA clone pNL4-3 was excised with HindIII, and the resultant about 1.2 kb DNA fragment was inserted into the HindIII portion of the cloning vector pHSG398 (made by Takara Shuzo [JAPAN]) to prepare pNLH122. This pNLH122 was excised with BqlII and HindIII, and the resultant about 1.03 kb DNA fragment was inserted into M13mp19 (made by Takara Shuzo) cleaved with BamHI and HindIII, to prepare Gag19·(Bg-H). The sequence GAG immediately before the initiation codon (ATG) of gag gene on Gag19·(Bg-H) was converted into CAT by means of oligonucleotide-directed in vitro mutagenesis system Version 2 (made by Amersham [UK]) and prepared Gag19·(Nde) into which NdeI site was newly introduced. Gag19·(Nde) was excised with NdeI and PstI, and the resultant 0.63 kb DNA fragment was inserted into pT7-7 cleaved with NdeI and PstI to prepare pTG541. Furthermore, pPG912 and pPG922 prepared in the Example 10 were excised with PstI, and the resultant about 1.2 kb DNA fragments were respectively inserted in the PstI portion of pTG541 and linked in a desirable direction with same, and the thus constructed plasmids were referred to a pTG591 and pTG592, respectively. In pTG591 and pTG592, the DNA fragments completely containing all the range from the initiation codon of gag gene under contpol of T7 promotor to the protease region of pol gene are linked. In pTG591, the expressed HIV protein is subjected to a process based on protease coexpressed through frameshifting, thus producing p17, p24 and p15 in large quantities. In pTG592, the expressed HIV protein is subjected to a process based on protease coexpressed without frameshifting, thus producing p17 and p24 in large quantities.

Strain JM103 was used as the host for constructing plasmid, and strain BL21 (DE3) was used as the host for expression of proteins.

EXAMPLE 15

Construction of a Vector Highly Expressing Matrix Protein of AIDS Virus

First, pTG591 prepared in the Example 14 was excised with NsiI and ApaI, and after treatment with S1 nuclease, and caused to make self-linkage. When the N-terminus side from the Nsi portion of gag gene and the C-terminus side from the Apa portion are fused in-frame, Gag protein and Gag-Pol protein lacking the portion from the middle of p24 to the middle of p15 are expressed, and are estimated to be subjected to a process based on protease contained in the Gag-Pol protein, thus producing p17. From among clones obtained in the above-mentioned operation, the clone expressing the activity for processing p55 Gag protein and producing p17 in a large quantity was selected and named pTG691.

After excising with BclII, pTG591 was treated with T4 DNA polymerase, and then further excised with PstI. The resultant about 0.52 kb DNA fragment was collected. On the other hand, pTG591 was treated sequentially with NsiI, S1 nuclease, and PstI, and the resultant about 2.9 kb DNA fragment was collected. From among many clones obtained by linking these two kinds of DNA fragments, the clone expressing the activity for processing p55 Gag protein and producing p17 in a large quantity was selected and named pTG691.

pTG591 was excised with SphI and ApaI, and after treatment with T4 DNA polymerase, caused to make self-linkage to prepare pTG171.

pTG592 was excised with SihI and ApaI, and after treatment with T4 DNA polymerase, caused to make self-linkage to prepare pTG172.

Gag19·(Nde) prepared in the Example 14 was excised with EcoRI and PstI, and the resultant 0.76 kb DNA fragment was inserted into M13mp18 cleaved with EcoRI and PstI to prepare Gag18·(Bg-P). The 133rd codon CCT of gag gene on Gag18·(Bg-P) was converted with in vitro mutagenesis into TAA, to prepare Gag18·TAA having the termination codon inserted immediately after the region encoding p17. Gag18·TAA was excised with NdeI and PstI, and the resultant 0.63 kb DNA fragment was inserted into pT7-7 cleaved with NdeI and PstI to prepare pTG52.

The defective Gag protein and Gap-Pol protein were subjected to processing, thus producing p17 in a large quantity, through frameshifting in pTG691 and pTG171, and by protease expressing without frameshifting in pTG681 and pTG172. In addition, pTG52 directly produces in a large quantity p17 not requiring processing after translation.

Strain JM103 was used as the host for constructing plasmid, and strain BL21 (DE3) was used as the host for protein expression.

EXAMPLE 16

Extraction of p17

The transformant clone BL21 (DE3)/pTG171 was cultured at 37° C. for 18 hours in LB medium containing 20 μm/ml ampicillin, then 1/100 polume was added to fresh LB medium (containing 20 μm/ml ampicillin) and cultured at 37° C. When the OD600$_{nm}$ of the medium reached 0.5, 1 mM IPTG was added, and culture was continued at 37° C. for five hours. Bacterial cells were collected through centrifugation (5,000 rpm, 10 minutes), suspended in 1/50 volume of 15 mM sodium phosphate [pH 6.7], and after ultrasonic treatment (six 30-second bursts, 19.5 kHz, 300 W), the supernatant liquid obtained through centrifugation (19,000 rpm, 60 minutes) was separated as crude extraction liquid.

Rough purification of p17: Ammonium sulfate was added to the crude extraction liquid so as to give 40% saturation, and after stirring, the mixture was subjected to centrifugation (16,000 rpm, 20 minutes). Ammonium sulfate was added to the supernatant liquid thus obtained so as to give 80% saturation, and after stirring, the mixture was subjected to centrifugation (16,000 rpm, 20 minutes). The resultant precipitate was dissolved into 15 mM sodium phosphate buffer [pH 6.7], and dialyzed against same buffer.

Purification of p17: The dialyzed sample was applied to a S-sepharose (made by Pharmacia [Sweden]) equilibrated with 15 mM sodium phosphate [pH 6.7]. The sample was then eluted with sodium chloride gradient from 0 to 1M. Fractions containing p17 were pooled and diluted to twice with 15 mM sodium phosphate. This fraction was applied to a MonoS column (made by Pharmacia) equilibrated with same buffer. The sample was then eluted with sodium chloride gradient of from 0 to 1M, fractions containing p17 were pooled, and diluted to five times with 20 mM sodium phosphate [pH 7.0 ] and 10 mM 2-mercaptoethanol. The resultant diluted sample was applied to a hydroxyapatite column (KB column, made by Koken, Ltd. [Japan]), and eluted with sodium phosphate gradient of from 15 to 700 mM. The yield of purified p17 per liter of transformant culture liquid was about 4mg. Purified p17, from which methionine residue at N-terminal had been removed, was not subjected myristylation and had an N-terminal amino acid sequence of: Gly-Ala-Arg-Ala-Ser-Val-Leu-Ser-Gly-Gly-Glu-Leu-Asp-Lys-Trp . . . (SEQ ID NO:4), thus agreeing with the amino acid sequence predicted from the nucleotide sequence.

EXAMPLE 17

Construction of Expression Plasmid Carrying Nef Gene of HIV-1

HIV-1 proviral DNA clone pNL4-3 was excised with HindIII, and the resultant about 1.5 kb DNA fragment was inserted into the HindIII portion of the cloning vector pHSG398 to prepare pNLH152. This pNLH152 was excised with HindIII and XhoI. The resultant about 0.72 kb XhoI-HindIII fragment was inserted into the expression vector pUR292 (The EMBO Journal, 2 (2): 1791–1794, 1983) cleaved with SalI and HindIII to prepare pNF102. This pNF102 was excised with BamHI and HindIII, and the resultant about 0.72 kb BamHI—HindIII fragment was inserted into the expression vector pT7-7 cleaved with BamHI and HindIII to prepare pTF103. This pTF103 was then cleaved with BamHI, and after treatment with T4 DNA polymerase, caused to make self-linkage to prepare pTN104.

The above-mentioned pNF102 highly expressed chimaera protein comprising β-galactosidase and a region of from the 35th to 206th (C-terminal) amino acids of HIV-1 Nef protein. The above-mentioned pTN104 highly expressed chimaera protein in which a peptide consisting of 11 amino acids derived from multi-cloning site of pT7-7 was added to the N-terminal of the region covering from the 35th to the 206th amino acids of Nef protein. These chimaera proteins specifically reacted with serum from HIV-1 carrier in Western blotting. Strain JM103 and strain UT481 were used in pNF102, and strain BL21 (DE3) was used in pTF104, as the hosts for expression.

EXAMPLE 18

Construction of a Vector Highly Expressing HIV-1 Nef Protein

First, pNLH152 was excised with HindIII and HincII, and the resultant about 0.96 kb HincII—HindIII fragment was inserted into M13 m19 cleaved with HincII and HindIII to prepare Nef19·(Hc-H). The sequence AAG immediately before the initiation codon (ATG) of nef gene on Nef19·(Hc-H) was converted into CAT by means of in vitro mutagenesis to prepare Nef19·(Nde) into which the Nde site was introduced anew. Nef19·(Nde) was excised with NdeI and HindIII, and the resultant about 0.82 kb NdeI-HindIII was inserted into the expression vector pT7-7 cleaved with NdeI and HindIII to prepare pT7-Nef. By introducing pT7-Nef into strain BL21 (DE3), Nef protein accounting for more than 10% of the entire bacterial protein was expressed and accumulated.

EXAMPLE 19

Extraction and Purification of Nef Protein

The transformant clone BL21 (DE3)/pT7-Nef (deposited at the National Institute of Bioscience and Human Technology, Ministry of International Trade and Industry, 1-3 Higashi 1-chome, Yatabe-machi, Tsukuba-gun, Ibaragi-ken, Japan on Mar. 28, 1994 and bears accession no. FERM BP-4621) was cultured at 37° C. for 18 hours in LB medium containing 20 μg/ml ampicillin, then 1/100 volume was added to fresh LB medium (containing 20 ug/ml ampicillin) and the mixture was cultured at 370 C. When the $OD600_{nm}$ of the medium reached 1.0, 1 mM IPTG was added, and culture was further continued for five hours. Bacterial cells were collected through centrifugation (5,000 rpm, 10 minutes), suspended in 1/50 volume of 20 mM sodium phosphate, and after ultrasonic treatment (six 30-second bursts, 19.5 kHz, 300 W), the supernatant liquid resulting from centrifugation (19,000 rpm, 60 minutes) was separated as the crude extraction liquid.

Rough purification of Nef protein: Ammonium sulfate was added to the crude extraction liquid so as to give 35% saturation, and after stirring, the mixture was subjected to centrifugation (16,000 rpm, 20 minutes). The resultant precipitate was dissolved into 20 mM sodium phosphate buffer, and was then dialyzed against same buffer.

Purification of Nef protein: The dialyzed sample was applied to S-sepharose (made by Pharmacia [Sweden]) equilibrated with 20 mM sodium phosphate [pH 7.0]. The sample was then eluted with sodium chloride gradient of from 0 to 1M, the fractions containing Nef protein were pooled and was then dialyzed against 20 mM sodium phosphate [pH 7.0]. The sample was then applied to a hydroxyapatite column (KB column, made by Koken, Ltd.) and eluted with sodium phosphate gradient of from 20 to 700 mM. The fractions containing Nef protein were pooled and dialyzed against 20 mM tris HCl [ph 8.3]and 5 mM 2-mercaptoethanol. This sample was applied to a MonoQ column, and eluted with sodium chloride gradient of from 0 to 1 mM. The fractions containing Nef protein were pooled, thereby preparing purified Nef protein. The yield of purified Nef protein per liter of transformant culture liquid was about 7 mg.

Nef protein mass produced with *E. coli* and purified, from which N-terminal methionine residue had been removed, was not subjected to myristoylation, and showed an N-terminal amino acid sequence of: Gly-Gly-Lys-Trp-Ser-Lys-Ser-Ser-Val-Ile-Gly-Trp-Pro-Ala-Val . . . (SEQ ID NO:5), thus agreeing with the amino acid sequence predicted from the nucleotide sequence.

EXAMPLE 20

Diagnosis of HIV-1 Infection Using Purified Nef Protein

The purified Nef protein prepared in the Example 19 was electrophoresed on a polyacrylamide gel in accordance with the procedures described in Example 2, and was blotted onto a nitrocellulose membrane. The membrane was then immersed in a 3 W/V % gelatin solution for blocking. Subsequently, the presence of an antibody against the HIV-1 Nef protein was investigated in the sera of human HIV-1 carriers (7 subjects) using a Western blot technique. Healthy adults (9 subjects) were similarly investigated. The result is shown in Table 2.

The sera of 6 from among 7 HIV-1 carriers positively reacted with Nef protein. This suggests that it is possible to make specific detection and diagnosis of the presence of HIV-1 infection by using purified HIV-1 Nef protein prepared from *Escherichia coli* according to the present invention.

TABLE 2

| Diagnosis of HIV-1 infection by Western blotting, using purified Nef protein | | |
|---|---|---|
| | Subject | Reactivity* |
| Human serum of HIV-1 carrier | 1 | +** |
| | 2 | + |
| | 3 | + |
| | 4 | + |
| | 5 | + |
| | 6 | + |
| | 7 | ± |
| Human serum of healthy adult | 1 | + |
| | 2 | ± |
| | 3 | − |
| | 4 | − |
| | 5 | − |
| | 6 | − |
| | 7 | − |
| | 8 | − |
| | 9 | − |

*Specific immunological reaction against purified Nef protein.
**Reactivity was measured by the Western blot technique. Shown are positive (+) and negative (−) reactions.

INDUSTRIAL APPLICABILITY

The present invention is applicable to the field of manufacture of medical supplies and diagnostic agents based on genetic engineering, and as a reagent for research, to such fields as molecular biology, vipology, medical science, pharmacology, veterinary science, and immunology.

We claim:

1. A method for preparing a plasmid pNF102 having the ability of expressing an HIV nef gene encoding amino acids 35 to 206 of Nef protein in an *E. coli* UT481 or JM103 recipient cell, which comprises:

preparing a recombinant DNA pNLH152 by inserting Hind III DNA fragment of about 1.5 kb length from a HIV DNA clone into the Hind III-cleaved site of a cloning vector pHSG398;

preparing a cDNA fragment of said HIV nef gene by isolating Xho I-Hind III DNA fragment of about 0.72 kb length from the pNLH152; and inserting the cDNA fragment into the Sal I and Hind III-cleaved site of a plasmid pUR292 so that the cDNA fragment is operably linked with a lacZ gene under contpol of a lacUV5 promoter.

2. A method for preparing a plasmid pTF104 having the ability of expressing an HIV nef gene encoding amino acids 35 to 206 of Nef protein in an *E. coli* BL21(DE3) recipient cell, which comprises:

preparing a cDNA fragment of said HIV nef gene by isolating Ban Hl-Hind III DNA fragment of about 0.72 kb length from the plasmid pNF102 of claim 1; and inserting the cDNA fragment into a Bam Hl and Hind III-cleaved site of plasmid pT7-7 to prepare a plasmid pTF103; and cleaving the DTF103 with BamHl, and then treating it with T4 DNA polymerase for self-linkage so that the cDNA fragment is operably linked with a T7 promoter.

3. A method for preparing a plasmid pT7-Nef having the ability of expressing an HIV nef gene encoding all 206 amino acids of Nef protein in an *E. coli* BL21(DE3) recipient cell, which comprises:

preparing a recombinant DNA pNLH152 by inserting Hind III DNA fragment of about 1.5 kb length from a HIV DNA clone into the Hind III-cleaved site of a cloning vector pHSG398;

preparing a recombinant DNA Nef19-(Hc-H) by inserting Hinc II-Hind III DNA fragment of about 0.96 kb length into a vector M13mp19;

introducing a new Nde I site into the Nef219-(Hc-H) by converting the sequence AAG immediately before the initiation codon ATG of the nef gene on the Nef219-(Hc-H) into GAT. thereby preparing a recombinant DNA Nef19(Nde);

preparing a cDNA fragment of said HIV nef gene by isolating Nde I-Hind III DNA fragment of about 0.82 kb length from the Nef19(Nde); and inserting the cDNA fragment into a Nde I and Hind III-cleaved site of plasmid pT7-7 so that the DNA fragment is operably linked with a T7 promoter.

4. A plasmid pNF102 having the ability of expressing an HIV nef gene encoding amino acids 35 to 206 of Nef protein in an *E. coli* UT481 or JM103 recipient cell, which consists of a cDNA fragment of said HIV nef gene and a plasmid pUR292 containing a lacz gene under contpol of a lacUV5 promoter, wherein said cDNA fragment is operably linked with the lacZ gene under control of the lacUV5 promoter.

5. A plasmid pTF104 having the ability of expressing an HIV nef gene encoding amino acids 35 to 206 of Nef protein in an *E. coli* BL21(DE3) recipient cell, which consists of a cDNA fragment of said HIV nef gene and a plasmid pT7-7 containing a T7 promoter, wherein said cDNA is operably linked with the T7 promoter.

6. A plasmid pT7-Nef having the ability of expressing an HIV nef gene encoding all 206 amino acids of Nef protein in an *E. coli* BL21(DE3) recipient cell, which consists of a cDNA fragment of said HIV nef gene and a plasmid pT7-7 containing a T7 promoter, wherein said cDNA is operably linked with the T7 promoter.

* * * * *